United States Patent
Okihara

(10) Patent No.: US 12,397,121 B2
(45) Date of Patent: Aug. 26, 2025

(54) SYRINGE CAP, SYRINGE ASSEMBLY, AND PREFILLED SYRINGE

(71) Applicant: TERUMO KABUSHIKI KAISHA, Tokyo (JP)

(72) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1009 days.

(21) Appl. No.: 17/481,928

(22) Filed: Sep. 22, 2021

(65) Prior Publication Data

US 2022/0008660 A1    Jan. 13, 2022

Related U.S. Application Data

(63) Continuation of application No. PCT/JP2019/012195, filed on Mar. 22, 2019.

(51) Int. Cl.
*A61M 5/32* (2006.01)
*A61M 5/28* (2006.01)
*A61M 5/31* (2006.01)

(52) U.S. Cl.
CPC ............ *A61M 5/3202* (2013.01); *A61M 5/28* (2013.01); *A61M 5/3134* (2013.01)

(58) Field of Classification Search
CPC .... A61M 5/3202; A61M 5/28; A61M 5/3134; A61M 5/5086; A61M 39/20; A61M 2005/3104; A61M 2005/3106
See application file for complete search history.

(56) References Cited

U.S. PATENT DOCUMENTS

| | | | |
|---|---|---|---|
| 10,369,083 B2 * | 8/2019 | Swisher | A61M 39/1011 |
| 2016/0151584 A1 | 6/2016 | Deleuil et al. | |
| 2017/0000955 A1 * | 1/2017 | McLoughlin | A61M 5/3134 |
| 2017/0143893 A1 * | 5/2017 | Hasumi | A61M 5/3202 |
| 2017/0232160 A1 * | 8/2017 | Cardwell | A61B 17/34 606/131 |
| 2019/0046736 A1 | 2/2019 | Okihara | |
| 2019/0217020 A1 | 7/2019 | Okihara | |

FOREIGN PATENT DOCUMENTS

| | | |
|---|---|---|
| JP | 2016524981 A | 8/2016 |
| WO | 2017179313 A1 | 10/2017 |
| WO | 2018061948 A1 | 4/2018 |

OTHER PUBLICATIONS

International Search Report (PCT/ISA/210) with translation and Written Opinion (PCT/ISA/237) with translation mailed on Jun. 25, 2019, by the Japan Patent Office as the International Searching Authority for International Application No. PCT/JP2019/012195.

* cited by examiner

*Primary Examiner* — Michael J Tsai
*Assistant Examiner* — Kathleen Paige Farrell
(74) *Attorney, Agent, or Firm* — Buchanan Ingersoll & Rooney PC

(57) ABSTRACT

A syringe assembly of a prefilled syringe includes a syringe cap. A tapered section of a second tubular section constituting this cap has, on an outer peripheral surface of the tapered section, a plurality of stepped sections continuously arranged along a center axis of a cover member, so as to gradually increase a protruding amount of the tapered section from an outer peripheral surface of an annular peripheral wall section toward a vicinity of an outer edge of an opening of a first tubular section.

19 Claims, 7 Drawing Sheets

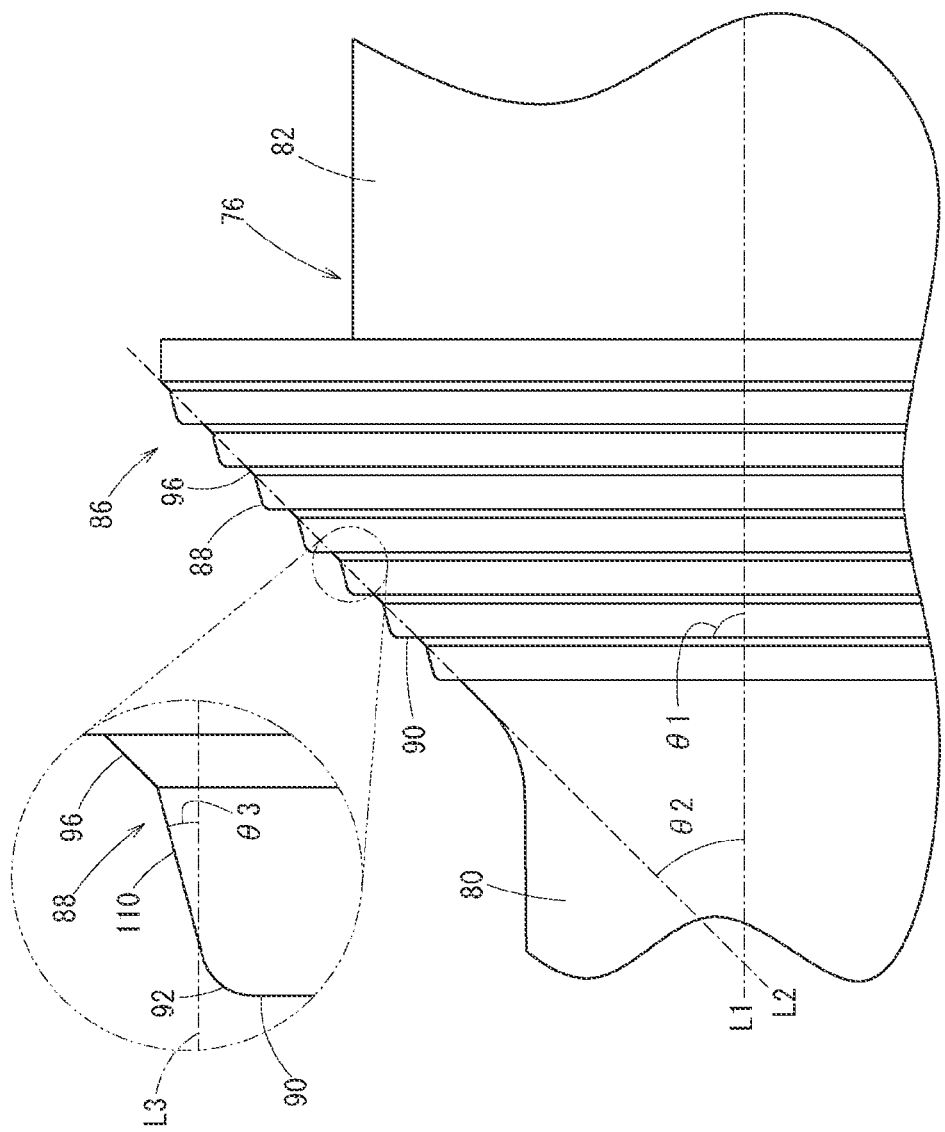

SYRINGE CAP, SYRINGE ASSEMBLY, AND PREFILLED SYRINGE

CROSS-REFERENCES TO RELATED APPLICATIONS

This application is a continuation of International Application No. PCT/JP2019/012195 filed on Mar. 22, 2019, the entire content of which is incorporated herein by reference.

FIELD OF THE DISCLOSURE

The present disclosure generally relates to a syringe cap, a syringe assembly, and a prefilled syringe, in which the syringe cap is detachable from a syringe body that includes a body section capable of internally accommodating a drug, and a nozzle section protruding in a distal end direction from a distal end section of the body section and having a drug discharge port at a distal end.

BACKGROUND DISCUSSION

WO 2018/061948 A discloses a syringe cap including a cap body and a tubular cover member covering the cap body. The cap body has a mounting section that is mountable to a nozzle section of a syringe body, and a viewing section located on a distal end side from the mounting section. The cover member includes a substantially opaque first tubular section and a substantially transparent second tubular section extending in the distal end direction from an opening at a distal end of the first tubular section.

The cap body is at a first position where the viewing section is located in the first tube section in an unopened state of the syringe cap. At this time, the viewing section is substantially invisible (i.e., not visible). Whereas, when the mounting section of the syringe cap removed from the syringe body is brought close to the nozzle section, the cap body is displaced from the first position to a second position where the viewing section protrudes in the distal end direction from the distal end of the first tubular section, by being pushed in the distal end direction by the nozzle section. That is, the viewing section becomes substantially visible, which makes it possible to discriminate between an unopened state and an opened state of the syringe cap.

FIGS. 38 to 40B of WO 2018/061948 A describe a configuration of a syringe cap in which a tapered section inclined outward in a proximal end direction is provided at a portion on the distal end side from the first tubular section on an outer peripheral surface of the second tubular section. An outer peripheral surface of the tapered section is continuously inclined at a constant angle with respect to a center line of the cover member from a distal end to a proximal end of the tapered section, which makes it possible to prevent the syringe cap from being caught by an opening edge section of an insertion tube when the syringe assembly with the syringe cap mounted to the syringe body is inserted into the insertion tube for conveyance.

However, in the syringe cap as described in WO 2018/061948 A, when the tapered section is viewed from just beside (in a direction orthogonal to a center axis of the syringe cap) in an unopened state of the syringe cap, there is a possibility that the viewing section of the cap body at the first position may be visible since light is refracted in the proximal end direction of the syringe cap on the outer peripheral surface of the tapered section.

SUMMARY

A syringe cap, a syringe assembly, and a prefilled syringe are disclosed in which the syringe cap can be rather easily inserted into an insertion tube for conveyance, and an unopened state and an opened state of the syringe cap can be rather easily and reliably discriminated.

In accordance with one aspect of the present disclosure, a syringe cap detachable from a syringe body is disclosed, the syringe body including: a body section capable of internally accommodating a drug; and a nozzle section protruding in a distal end direction from a distal end section of the body section and having a drug discharge port at a distal end. The syringe cap includes a cap body and a cover member having a tubular shape and covering the cap body. The cap body has a mounting section including a sealing section that liquid-tightly seals the drug discharge port, and being mountable to the nozzle section; and a viewing section located on a distal end side from the mounting section. The cover member includes: an engagement section provided on an inner peripheral surface of the cover member, and configured to engage with the cap body to prevent detachment of the cap body in a proximal end direction from the cover member; a first tubular section being substantially opaque, and having an opening at a distal end and a first space capable of internally housing the viewing section; and a second tubular section extending in a distal end direction from the opening of the first tubular section. The second tubular section includes: an annular peripheral wall section extending in a distal end direction from the opening of the first tubular section and having an outer diameter smaller than an outer diameter of the first tubular section; a distal end wall provided at a distal end of the annular peripheral wall section; a second space defined by the annular peripheral wall section, the distal end wall, and the opening of the first tubular section; and a tapered section protruding from an outer peripheral surface of the annular peripheral wall section toward a vicinity of an outer edge of the opening of the first tubular section so as to be inclined outward in a proximal end direction. At least the tapered section and the annular peripheral wall section of the second tubular section are substantially transparent. The cap body can displace, along a center axis of the cover member in the cover member, from a first position where the viewing section is located in the first space of the first tubular section to a second position where the viewing section protrudes in a distal end direction from the distal end of the first tubular section to be arranged in the second space. An outer peripheral section of the viewing section is substantially invisible when the cap body is at the first position, and the outer peripheral section of the viewing section becomes visible when the cap body is at the second position. The sealing section is capable of liquid-tightly sealing the nozzle section in a state where the cap body is located at the first position. In a state where the cap body is arranged at the first position, when the mounting section of the syringe cap removed from the syringe body is brought close to the nozzle section of the syringe body, the mounting section is pushed in a distal end direction by the nozzle section of the syringe body so as to displace the cap body from the first position to the second position. The tapered section has, on an outer peripheral surface of the tapered section, a plurality of stepped sections continuously arranged along the center axis of the cover member, so as to gradually increase a protruding amount of the tapered section from an outer peripheral surface of the annular peripheral wall section toward a vicinity of the outer edge of the opening of the first tubular section.

In accordance with another aspect of the present disclosure, a syringe assembly is disclosed, which includes: the syringe cap described above; and a syringe outer tube constituting the syringe body and being capable of accommodating a drug.

In accordance with a further aspect of the present disclosure, a prefilled syringe is disclosed, which includes: the syringe assembly described above; a drug filled in the syringe outer tube; and a gasket liquid-tightly slidable in the syringe outer tube in an axial direction.

According to the present disclosure, in an unopened state of the syringe cap, the cap body is at the first position where the viewing section is located in the first space of the substantially opaque first tubular section. Further, the tapered section of the second tubular section has a plurality of stepped sections on the outer peripheral surface of the tapered section of the second tubular section. As a result, when the tapered section is viewed from just beside, a refractive index of light on the outer peripheral surface of the tapered section can be reduced as compared with a case where the plurality of stepped sections are not provided on the outer peripheral surface of the tapered section. Therefore, the viewing section of the cap body at the first position can be made less visible when a user views the tapered section from just beside in an unopened state of the syringe cap.

Whereas, when the mounting section of the syringe cap removed from the syringe body is brought close to the nozzle section, the cap body is displaced from the first position to the second position where the viewing section is located in the second space of the substantially transparent second tubular section. In this state, the user can visually recognize the viewing section. Therefore, even in a case where the syringe cap once removed from the syringe body is remounted to the syringe body, the user can discriminate between the unopened state and the opened state of the syringe cap.

Further, the plurality of stepped sections are continuously arranged along a center axis of the cover member such that a protruding amount of the tapered section gradually increases from the outer peripheral surface of the annular peripheral wall section toward a vicinity of the outer edge of the opening of the first tubular section, which can help prevent the tapered section from being caught by the opening edge section of the insertion tube, when the syringe assembly (prefilled syringe) with the syringe cap mounted to the syringe body is inserted into the insertion tube for conveyance. Therefore, the syringe assembly (prefilled syringe) can be rather easily inserted into the insertion tube for conveyance.

In accordance with an aspect, a syringe cap is disclosed configured to be detachable from and attachable to a syringe body, the syringe cap comprising: a cap body, the cap body includes: a mounting section including a sealing section configured to seal a drug discharge port on the syringe body and configured to be mounted to a nozzle section of the syringe body; and a viewing section located on a distal end side from the mounting section; a cover member having a tubular shape and covering the cap body, the cover member includes: an engagement section provided on an inner peripheral surface of the cover member, and the cover member being configured to engage with the cap body; a first tubular section having an opening at a distal end and a first space capable of internally housing the viewing section; and a second tubular section extending in a distal end direction from the opening of the first tubular section; the second tubular section includes: an annular peripheral wall section extending in a distal end direction from the opening of the first tubular section and having an outer diameter smaller than an outer diameter of the first tubular section; a distal end wall provided at a distal end of the annular peripheral wall section; a second space defined by the annular peripheral wall section, the distal end wall, and the opening of the first tubular section; and a tapered section protruding from an outer peripheral surface of the annular peripheral wall section toward a vicinity of an outer edge of the opening of the first tubular section so as to be inclined outward in a proximal end direction; and the tapered section has, on an outer peripheral surface of the tapered section, a plurality of stepped sections continuously arranged along the center axis of the cover member, so as to gradually increase a protruding amount of the tapered section from an outer peripheral surface of the annular peripheral wall section toward a vicinity of the outer edge of the opening of the first tubular section.

In accordance with another aspect, a syringe assembly is disclosed, the syringe assembly comprising: syringe body, the syringe body including a body section configured to accommodate a drug, and a nozzle section protruding in a distal end direction from a distal end section of the body section and having a drug discharge port at a distal end; and a syringe cap configured to be detachable from and attachable to the syringe body, the syringe cap comprising: a cap body, the cap body includes: a mounting section including a sealing section configured to seal a drug discharge port on the syringe body and configured to be mounted to a nozzle section of the syringe body; and a viewing section located on a distal end side from the mounting section; a cover member having a tubular shape and covering the cap body, the cover member includes: an engagement section provided on an inner peripheral surface of the cover member, and the cover member being configured to engage with the cap body; a first tubular section having an opening at a distal end and a first space capable of internally housing the viewing section; and a second tubular section extending in a distal end direction from the opening of the first tubular section; the second tubular section includes: an annular peripheral wall section extending in a distal end direction from the opening of the first tubular section and having an outer diameter smaller than an outer diameter of the first tubular section; a distal end wall provided at a distal end of the annular peripheral wall section; a second space defined by the annular peripheral wall section, the distal end wall, and the opening of the first tubular section; and a tapered section protruding from an outer peripheral surface of the annular peripheral wall section toward a vicinity of an outer edge of the opening of the first tubular section so as to be inclined outward in a proximal end direction; and the tapered section has, on an outer peripheral surface of the tapered section, a plurality of stepped sections continuously arranged along the center axis of the cover member, so as to gradually increase a protruding amount of the tapered section from an outer peripheral surface of the annular peripheral wall section toward a vicinity of the outer edge of the opening of the first tubular section.

BRIEF DESCRIPTION OF THE DRAWINGS

FIG. 7 is a partially omitted enlarged view of a tapered section according to a modification.

DETAILED DESCRIPTION

Set forth below with reference to the accompanying drawings is a detailed description of embodiments of a syringe cap, a syringe assembly, and a prefilled syringe, in which the syringe cap is detachable from a syringe body that includes a body section capable of internally accommodating a drug, and a nozzle section protruding in a distal end direction from a distal end section of the body section and having a drug discharge port at a distal end. Note that since embodiments described below are preferred specific examples of the present disclosure, although various technically preferable limitations are given, the scope of the present disclosure is not limited to the embodiments unless otherwise specified in the following descriptions. In the following description of the prefilled syringe and components of the prefilled syringe, the left side in FIG. 1 is referred to as a "distal end", and the right side is referred to as a "proximal end".

Figure 1:
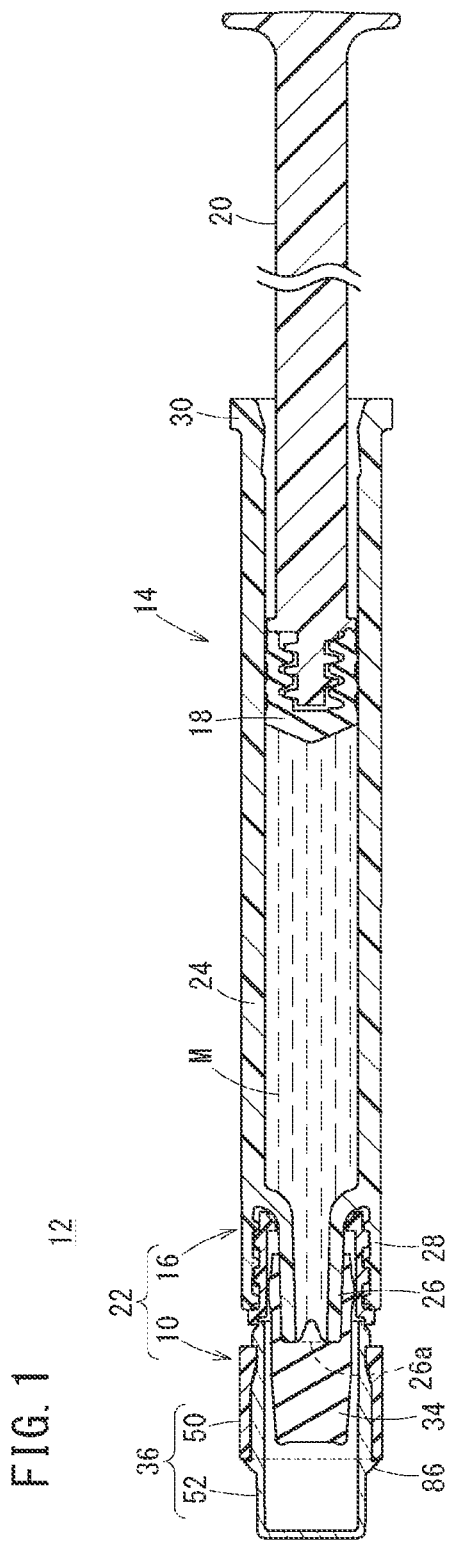
FIG. 1 is a longitudinal cross-sectional view of a prefilled syringe according to an embodiment of the present disclosure.

As illustrated in FIG. 1, a prefilled syringe 12 includes a syringe body 14 and a syringe cap 10 (hereinafter, may be simply referred to as a "cap 10") detachably attachable to the syringe body 14. The syringe body 14 includes a syringe outer tube 16, a gasket 18 slidably inserted into the syringe outer tube 16, and a plunger 20 connected to the gasket 18. In the present embodiment, the syringe outer tube 16 and the cap 10 constitute a syringe assembly 22, and the prefilled syringe 12 is assembled by inserting the gasket 18 connected with the plunger 20 in a state where the syringe outer tube 16 of the syringe assembly 22 is filled with a drug M.

The syringe outer tube 16 can include: a cylindrical body section 24 extending in an axial direction; a hollow nozzle section 26 projecting in the distal end direction from a distal end section of the body section 24; a syringe-side connecting section 28 provided on an outer peripheral side of the nozzle section 26; and a flange section 30 provided at a proximal end section of the body section 24. The body section 24, the nozzle section 26, the syringe-side connecting section 28, and the flange section 30 are integrally formed (i.e., connected together so as to make up a single complete piece or unit).

Figure 2:
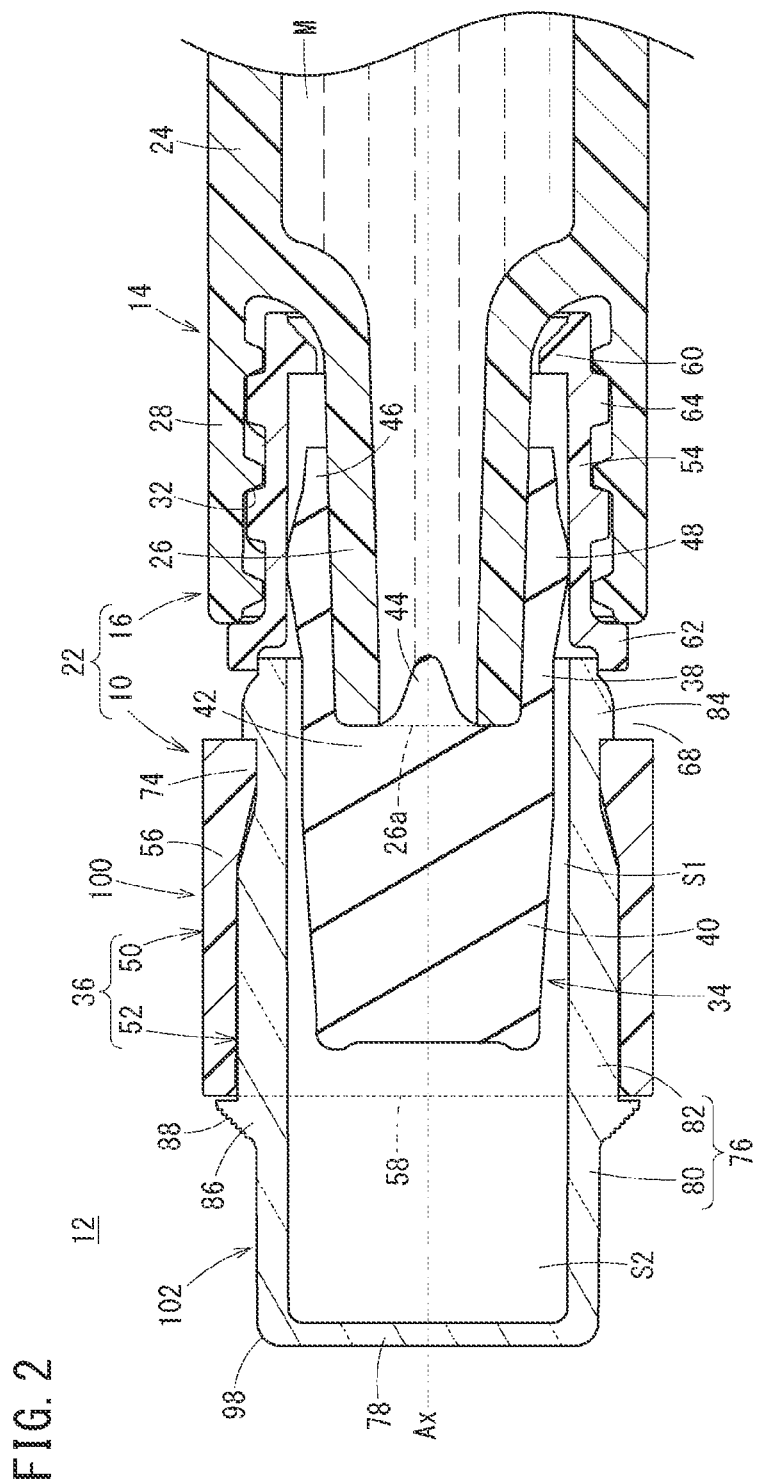
FIG. 2 is a partially omitted enlarged cross-sectional view of a distal end side of the prefilled syringe of FIG. 1.

As illustrated in FIG. 2, the nozzle section 26 is a cylindrical member provided with a drug discharge port 26a at a distal end, and is configured as a luer connector. The syringe-side connecting section 28 is a lock adapter that projects from a distal end section of the body section 24 to a distal end side concentrically with the nozzle section 26, and has a female screw section 32 formed on an inner peripheral surface. To the syringe-side connecting section 28, the cap 10, an injection needle, and the like are detachably attachable.

A constituent material of the syringe outer tube 16 is not particularly limited, but is preferably form by, for example, polyolefin such as polypropylene, polyurethane, polyethylene, cyclic polyolefin, or polymethylpentene 1, a resin material such as polyester, nylon, polycarbonate, polymethyl methacrylate (PMMA), polyetherimide (PEI), polyethersulfone, polyether ether ketone (PEEK), fluororesin, polyphenylene sulfide (PPS), or a polyacetal resin (POM), a metal material such as stainless steel, glass, or the like.

In FIG. 1, the gasket 18 is liquid-tightly slidable in the syringe outer tube 16 in an axial direction, and feeds the drug M filled in the syringe outer tube 16. A distal end of the plunger 20 is connected to the gasket 18.

Figure 3:
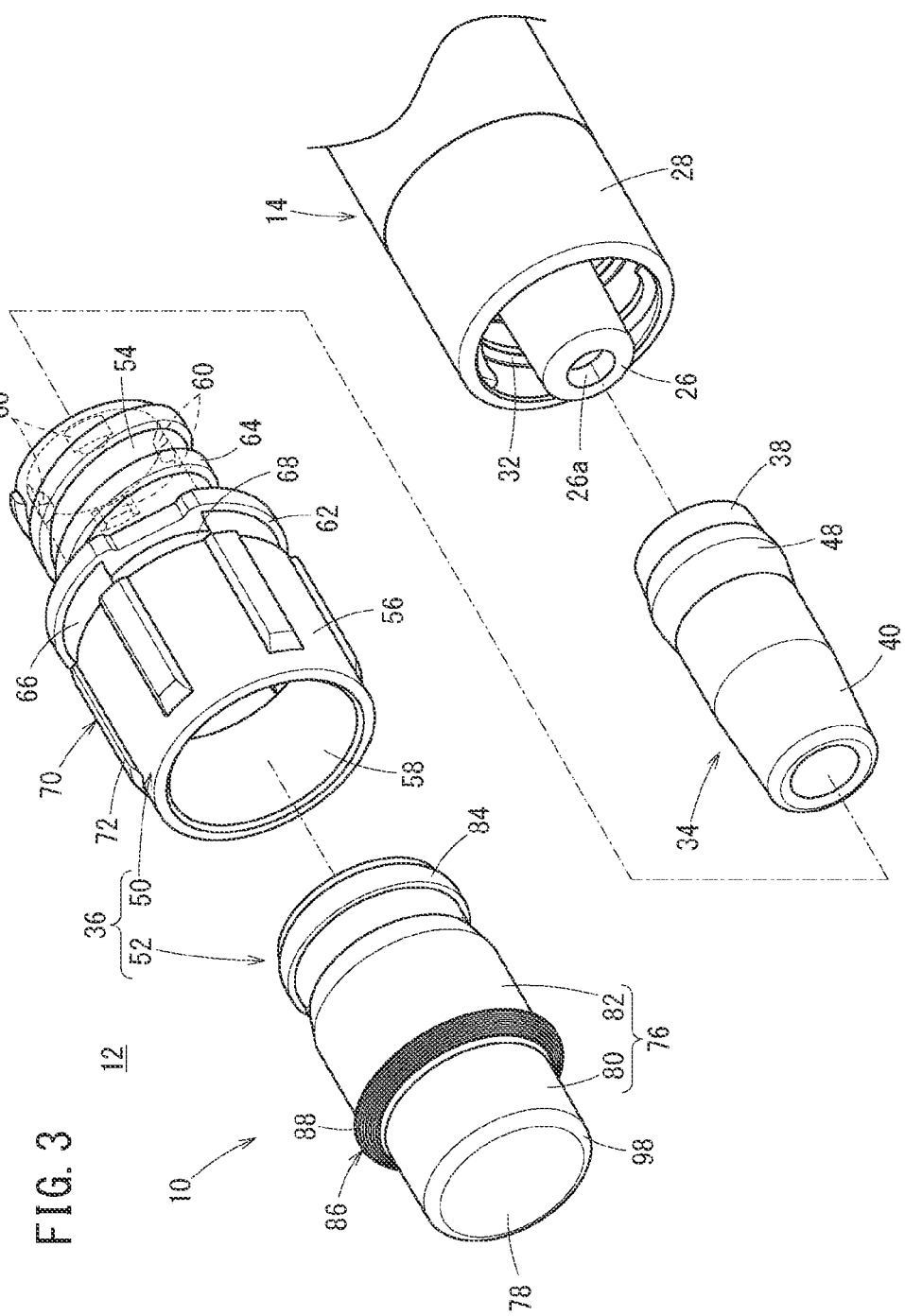
FIG. 3 is an exploded perspective view of FIG. 2.

As illustrated in FIGS. 2 and 3, the cap 10 includes a cap body 34 that closes the drug discharge port 26a of the nozzle section 26 in an unopened state, and a tubular cover member 36 that covers the cap body 34.

Examples of a constituent material of the cap body 34 can include rubber, a synthetic resin elastomer, and the like. Examples of the rubber can include isoprene rubber, butyl rubber, latex rubber, and silicone rubber. As the synthetic resin elastomer, for example, a styrene elastomer, an olefin elastomer, or the like can be used.

The cap body 34 includes a mounting tube section 38 (mounting section) and a viewing section 40 (distal end extending section) extending the distal end direction from a distal end of the mounting tube section 38. The mounting tube section 38 includes a sealing section 42 that is located at a distal end section of the mounting tube section 38 and is capable of liquid-tightly sealing the drug discharge port 26a, and a raised section 44 raised from the sealing section 42. The sealing section 42 seals the drug discharge port 26a by abutting on a distal end section of the nozzle section 26, specifically, a distal end surface of the nozzle section 26 or a side peripheral surface of the distal end section of the nozzle section 26.

The liquid-tightly sealing the drug discharge port 26a means that the drug M does not leak to the outside of the cap body 34. Therefore, even when the sealing section 42 abuts only on the side peripheral surface of the distal end section of the nozzle section 26, the sealing section 42 liquid-tightly seals the drug discharge port 26a.

At the proximal end section of an inner peripheral surface of the mounting tube section 38, an annular abutting protruding section 46 (abutting section) capable of abutting on a distal end section of the nozzle section 26 is provided. In a mounted state (unopened state) in which the cap body 34 is mounted to the nozzle section 26, the abutting protruding section 46 is in contact with an outer peripheral surface of the nozzle section 26 in a compressed and deformed state.

On an outer peripheral surface of the mounting tube section 38, an annular bulging section 48 is provided. The bulging section 48 is a section having a maximum outer diameter of the cap body 34. The bulging section 48 can be compressed and deformed by being sandwiched between the nozzle section 26 and a tubular connecting section 54, in the mounted state of the cap body 34.

The viewing section 40 is formed in a cylindrical shape. The viewing section 40 may be colored in a color that is relatively easily recognized by the user, such as red, for example. The coloring of the viewing section 40 may be performed by applying paint to an outer surface of the viewing section 40, or the cap body 34 may be made of rubber or synthetic resin colored in advance.

The cover member 36 includes a cap cover 50 and a distal end cover member 52.

The cap cover 50 is formed in a cylindrical shape and can be made of a resin material having no transparency (substantially opaque resin material). The cap cover 50 can include: the tubular connecting section 54 that is located at a proximal end section of cap cover 50 and is detachably attachable to a syringe side by screwing; a tubular section 56 extending in the distal end direction from a distal end of the tubular connecting section 54; and an opening 58 provided at a distal end of the tubular section 56 to expose the cap body 34 from the cap cover 50.

At a proximal end section of an inner peripheral surface of the tubular connecting section 54, a plurality of engagement claw sections 60 (engagement sections, engagement protrusions) extending radially inward are provided. The plurality of engagement claw sections 60 are intermittently provided along a circumferential direction of the tubular connecting section 54. Specifically, the plurality of engagement claw sections 60 are provided at equal intervals along the circumferential direction of the tubular connecting section 54. An inner diameter of a hole formed by projecting ends (inner end sections) of the plurality of engagement claw sections 60 is smaller than an outer diameter of a proximal end section of the mounting tube section 38 of the cap body 34.

In accordance with an exemplary embodiment, in each of the engagement claw sections 60, a surface directed in the distal end direction is a flat surface extending in a direction orthogonal to a center axis Ax of the cover member 36, and can be in contact with a proximal end surface of the cap body 34. Furthermore, the engagement claw section 60 has an inclined surface inclined inward in the distal end direction on the proximal end side of the engagement claw section 60. As a result, when the cap body 34 is inserted into the cap cover 50 from the proximal end of the cap cover 50, the cap body 34 can relatively easily get over the engagement claw section 60.

A proximal end of the tubular section 56 is provided with an insertion regulating section 62 that can abut on a distal end of the syringe-side connecting section 28. The insertion regulating section 62 helps regulate an insertion length of the tubular connecting section 54 between the syringe-side connecting section 28 and the nozzle section 26, by abutting on the distal end of the syringe-side connecting section 28. The tubular connecting section 54 is a cylindrical member provided concentrically with the cap cover 50, and has an outer peripheral surface provided with a male screw section 64 that can be screwed with the female screw section 32.

The tubular section 56 is formed in a size that allows a user to rather easily pick up the tubular section 56 with the fingers of the user. At a proximal end section of an outer peripheral surface of the tubular section 56, an annular recess 66 is formed. On a bottom surface of the annular recess 66, two through holes 68 are formed. In accordance with an exemplary embodiment, the two through holes 68 are opposed to each other.

On the distal end side from the annular recess 66 on the outer peripheral surface of the tubular section 56, an anti-slip section 70 functioning as a slip stopper for the user's fingers is formed. The anti-slip section 70 can be formed, for example, by providing a plurality of ribs 72 extending in an axial direction at equal intervals in a circumferential direction. In the present embodiment, for example, six (6) ribs 72 are provided in the circumferential direction of the tubular section 56. As described above, by setting the number of ribs 72 to six, moldability (injection molding accuracy) of the cap cover 50 can be improved.

On the distal end side of the annular recess 66 on an inner peripheral surface of the tubular section 56, a locking protruding section 74 to lock the distal end cover member 52 protrudes radially inward. Two locking protruding sections 74 are provided so as to be opposed to each other.

The distal end cover member 52 is formed to have a substantially U-shaped longitudinal cross section, and is to cover the cap body 34 such that the user operating the cap 10 together with the cap cover 50 cannot touch the cap body 34. That is, the distal end cover member 52 has a contact prevention function. The distal end cover member 52 also functions as a detachment prevention section that help prevent detachment of the cap body 34 from the opening 58 of the cap cover 50.

The distal end cover member 52 can include: an annular section 76 having a proximal end section fitted to the tubular section 56 of the cap cover 50 so as to project toward a distal end side from the opening 58 of the cap cover 50; and a distal end wall 78 provided at a distal end section of the annular section 76.

The annular section 76 can include an annular peripheral wall section 80 on the distal end side and a tubular extending inner tube section 82 extending in the proximal end direction from the annular peripheral wall section 80. In accordance with an exemplary embodiment, an inner diameter of the annular section 76 is constant from the distal end to the proximal end, and is larger than an outer diameter of the viewing section 40. In other words, an inner diameter of the distal end cover member 52 is substantially uniform from a distal end of the annular peripheral wall section 80 to a proximal end of the extending inner tube section 82.

The proximal end of the extending inner tube section 82 is in contact with the distal end of the tubular connecting section 54. At a portion corresponding to the annular recess 66 of the cap cover 50 on an outer peripheral surface of the extending inner tube section 82, an annular locking claw 84 to be in contact with the locking protruding section 74 of the cap cover 50 is provided. In accordance with an exemplary embodiment, an outer diameter of the locking claw 84 is larger than a separation interval of the locking protruding section 74.

On an outer peripheral surface of the annular peripheral wall section 80, there is provided a tapered section 86 protruding so as to be inclined outward in the proximal end direction toward the distal end of the tubular section 56 (in a vicinity of an outer edge of the opening 58 of the tubular section 56). The tapered section 86 annularly extends along a circumferential direction of the annular peripheral wall section 80.

Figure 4:
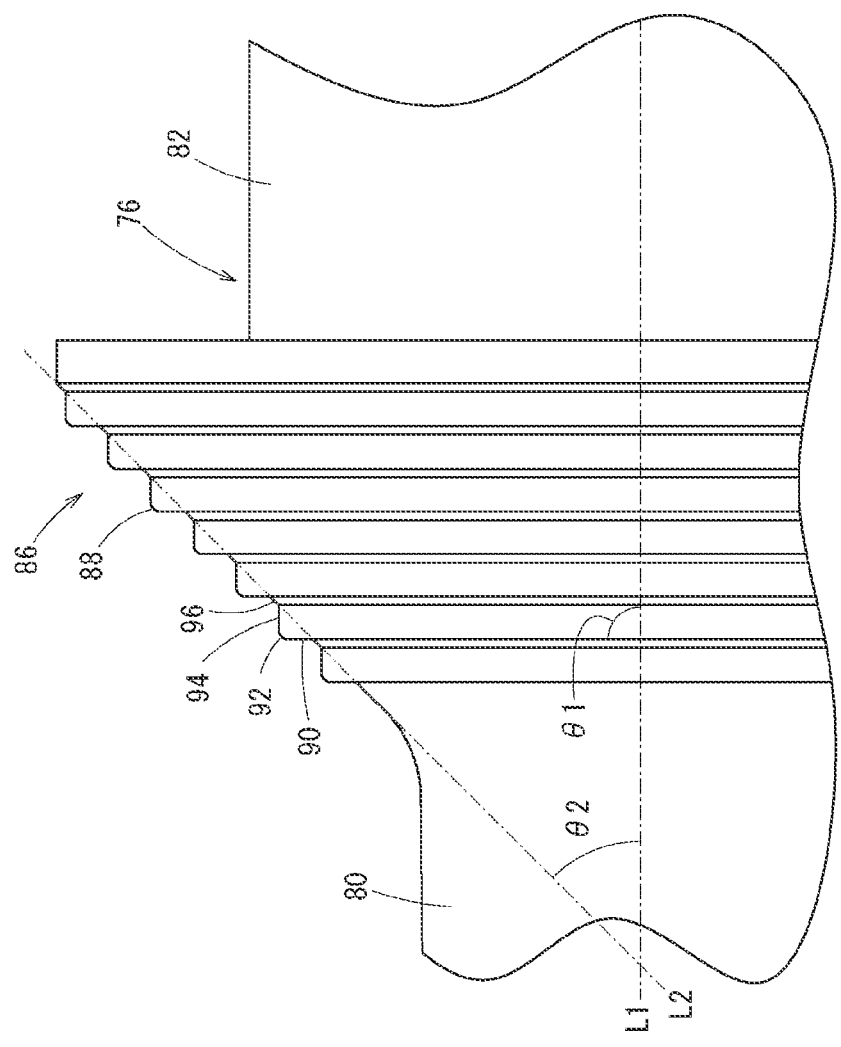
FIG. 4 is an enlarged view of a tapered section.

As shown in FIGS. 2 to 4, on an outer peripheral surface of the tapered section 86, a plurality of (for example, seven) stepped sections 88 are arranged continuously along the center axis Ax of the cover member 36 such that a protruding amount of the tapered section 86 gradually increases from the outer peripheral surface of the annular peripheral wall section 80 toward the distal end of the tubular section 56. Each stepped section 88 annularly extends along the circumferential direction of the annular peripheral wall section 80.

In accordance with an exemplary embodiment, each of the stepped sections 88 includes: a first surface 90; a bent section 92 located at an outer edge of the first surface 90; a second surface 94 extending in the proximal end direction from the bent section 92; and an inclined surface 96 extending while being inclined outward (radially outward) from a proximal end of the second surface 94 and continuing to an inner edge of the first surface 90 of the stepped section 88 adjacent on the proximal end side.

In accordance with an exemplary embodiment, an angle θ1 formed by the first surface 90 and a parallel straight line L1 parallel to the center axis Ax of the cover member 36 is larger than a taper angle θ2 formed by the parallel straight line L1 and a virtual straight line L2 passing through a distal end and a proximal end of the tapered section 86. The second surface 94 extends parallel to the center axis Ax of the cover member 36.

The angle θ1 is preferably set, for example, to 60° or more and 90° or less (i.e., 60° to 90°). In the present embodiment, for example, the angle θ1 is set to 90°. The taper angle θ2 can be preferably be set, for example, to 35° or more and 55° or less (i.e., 35° to 55°).

In accordance with an exemplary embodiment, the inclined surface 96 extends along the virtual straight line L2. In other words, the inclined surface 96 extends so as to overlap with the virtual straight line L2. Note that the inclined surface 96 may extend parallel to the virtual straight line L2. The bent section 92 has a curved surface protruding outward.

In accordance with an exemplary embodiment, a size, a number, a position, and a shape of the stepped section 88 can be appropriately set. For example, the stepped section 88 does not need to have the inclined surface 96. That is, the stepped section 88 may be formed such that a proximal end of the second surface 94 is continuous to an inner edge of the first surface 90 of the stepped section 88 adjacent on the proximal end side of the adjacent stepped section 88.

In FIGS. 2 and 3, between an outer edge of the distal end wall 78 and the annular peripheral wall section 80 (boundary section), a distal end curved surface 98 protruding outward is formed. A curvature radius of the distal end curved surface 98 can be preferably set, for example, to 0.3 mm or more and 1.0 mm or less (i.e., 0.3 mm to 1.0 mm).

In accordance with an exemplary embodiment, the distal end cover member 52 can be integrally molded using a resin material having transparency. In a case where the cap cover 50 is made of a resin material having transparency, the transparency of the distal end cover member 52 is set higher than the transparency of the cap cover 50, which allows the user to visually recognize the inside of the distal end cover member 52 from the outside of the cap 10 more clearly than the inside of the cap cover 50. In the present embodiment, the distal end cover member 52 can be colorless, but may be colored.

As illustrated in FIG. 2, such a cover member 36 includes the engagement claw section 60, a first tubular section 100, and a second tubular section 102. The engagement claw section 60 is provided on an inner peripheral surface of the cover member 36, and helps prevent detachment of the cap body 34 in the proximal end direction from the cover member 36, by engaging with the cap body 34. The first tubular section 100 has the opening 58 at a distal end and a first space S1 that can internally accommodate the viewing section 40. In accordance with an exemplary embodiment, the first tubular section 100 is substantially opaque. The first tubular section 100 includes the extending inner tube section 82 forming an inner peripheral section of the first tubular section 100, and the tubular section 56 forming an outer peripheral section of the first tubular section 100.

The second tubular section 102 is substantially transparent as a whole, and extends in the distal end direction from the opening 58 of the first tubular section 100. The second tubular section 102 includes the annular peripheral wall section 80, the distal end wall 78, a second space S2, and the tapered section 86. The annular peripheral wall section 80 extends in the distal end direction from the opening 58 of the first tubular section 100, and has an outer diameter smaller than an outer diameter of the first tubular section 100. The distal end wall 78 is provided at the distal end of the annular peripheral wall section 80. The second space S2 is defined by the annular peripheral wall section 80, the distal end wall 78, and the opening 58 of the first tubular section 100. The tapered section 86 protrudes so as to be inclined outward in the proximal end direction from the outer peripheral surface of the annular peripheral wall section 80 toward a vicinity of the outer edge of the opening 58 of the first tubular section 100.

In a prefilled syringe 12 as disclosed, in an unopened state of the cap 10, the cap body 34 is at a first position where the viewing section 40 is located in the first space S1 of the first tubular section 100. Specifically, the distal end of the cap body 34 is located in the proximal end direction from the opening 58 of the tubular section 56, and inside the extending inner tube section 82 of the distal end cover member 52. As a result, the outer peripheral section of the viewing section 40 can be hidden by the substantially opaque first tubular section (tubular section 56) and cannot be visually recognized from the outside. Further, the mounting tube section 38 is in a state of being mounted to the nozzle section 26, and the sealing section 42 of the mounting tube section 38 liquid-tightly seals the drug discharge port 26a of the nozzle section 26.

Figure 5A:
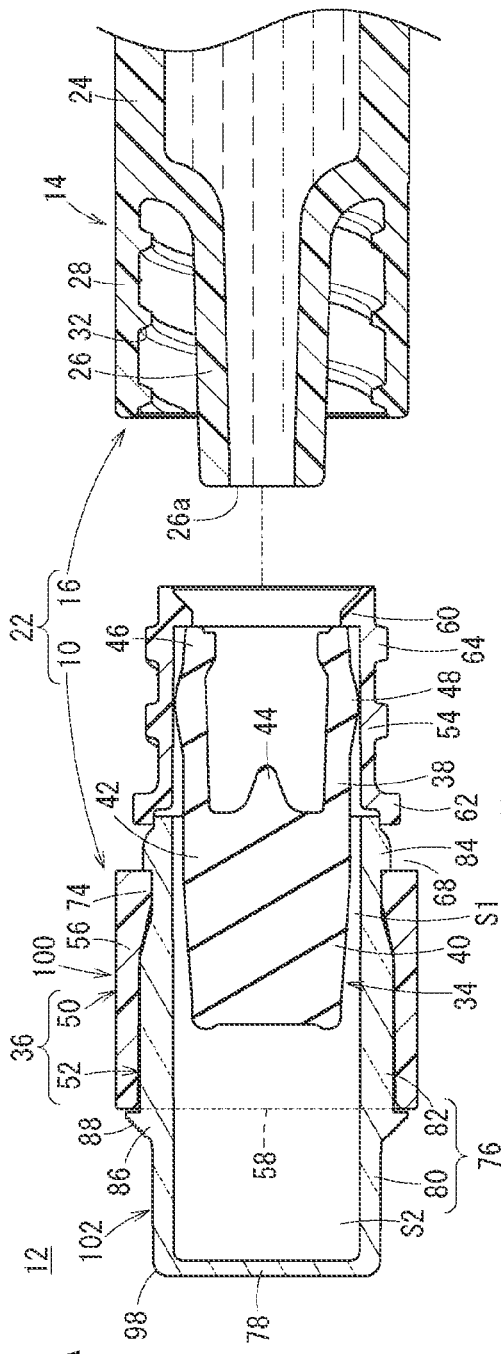
FIG. 5A is a first explanatory view of a recapping operation of a syringe cap.

In a case of opening the cap 10 from the syringe body 14, the cover member 36 is pulled out from the syringe outer tube 16 in a state where screwing between the male screw section 64 and the female screw section 32 is released, which causes the engagement claw section 60 of the tubular connecting section 54 to come into contact with the proximal end surface of the cap body 34. Then, the cap body 34 is pushed in the distal end direction by the tubular connecting section 54, and the mounting tube section 38 is detached from the nozzle section 26, which leads to opening of the cap 10 (see FIG. 5A).

In a case of recapping the opened cap 10 to the syringe outer tube 16, the distal end section of the nozzle section 26 of the syringe outer tube 16 is inserted into the tubular connecting section 54 from the opening 58 on the proximal end side of the tubular connecting section 54, which causes the distal end section of the nozzle section 26 to come into contact with the abutting protruding section 46 of the cap body 34.

Subsequently, when the cap cover 50 and the syringe outer tube 16 are brought relatively close to each other, by the abutting protruding section 46 of the cap body 34 abutting with the distal end section of the nozzle section 26, the cap body 34 at the first position is displaced in the distal end direction with respect to the cap cover 50 by being pushed by the nozzle section 26, and the viewing section 40 protrudes toward the distal end side from the opening 58 on the distal end side of the cap cover 50.

Figure 5B:
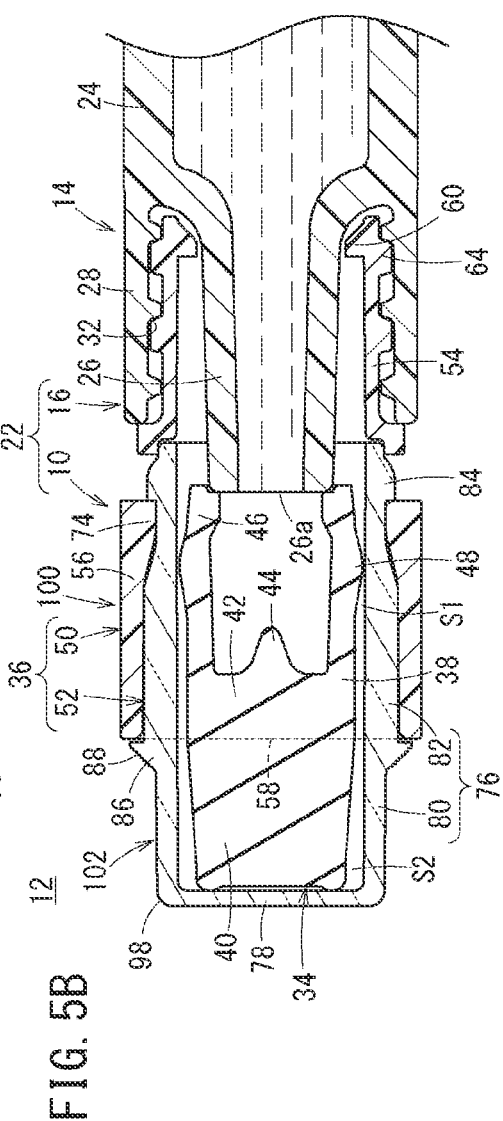
FIG. 5B is a second explanatory view of the recapping operation of the syringe cap.

Then, by screwing the male screw section 64 of the tubular connecting section 54 with the female screw section 32 of the syringe-side connecting section 28, the opened cap 10 is recapped (remounted) to the syringe outer tube 16. At this time, the cap body 34 is at the second position where the viewing section 40 is located in the second space S2 of the second tubular section 102 (on the distal end side from the opening 58 of the tubular section 56) (see FIG. 5B). Therefore, the outer peripheral section of the viewing section 40 can be visually recognized from the outside via the transparent second tubular section 102 (distal end cover member 52).

In this case, the cap 10, the syringe assembly 22, and the prefilled syringe 12 according to the present embodiment have the following effects.

In the cap 10, in an unopened state of the cap 10, the cap body 34 is at the first position where the viewing section 40 is located in the first space S1 of the substantially opaque first tubular section 100. Further, the tapered section 86 of the second tubular section 102 has a plurality of stepped sections 88 on the outer peripheral surface of the tapered section 86 of the second tubular section 102. As a result, when the tapered section 86 is viewed from just beside (a direction orthogonal to the center axis Ax of the cover member 36), a refractive index of light on the outer peripheral surface of the tapered section 86 toward the proximal end side of the cover member 36 can be reduced as compared with a case where the plurality of stepped sections 88 are not provided on the outer peripheral surface of the tapered section 86. Therefore, the viewing section 40 of the cap body 34 at the first position can be made less visible when the user views the tapered section 86 from just beside in an unopened state of the cap 10.

Whereas, when the mounting tube section 38 of the cap 10 removed from the syringe body 14 is brought close to the nozzle section 26, the cap body 34 is displaced from the first position to the second position where the viewing section 40 is located in the second space S2 of the substantially transparent second tubular section 102. In this state, the user can visually recognize the viewing section 40. Therefore, even in a case where the cap 10 once removed from the syringe body 14 is remounted to the syringe body 14, the user can discriminate between the unopened state and the opened state of the cap 10.

Figure 6:
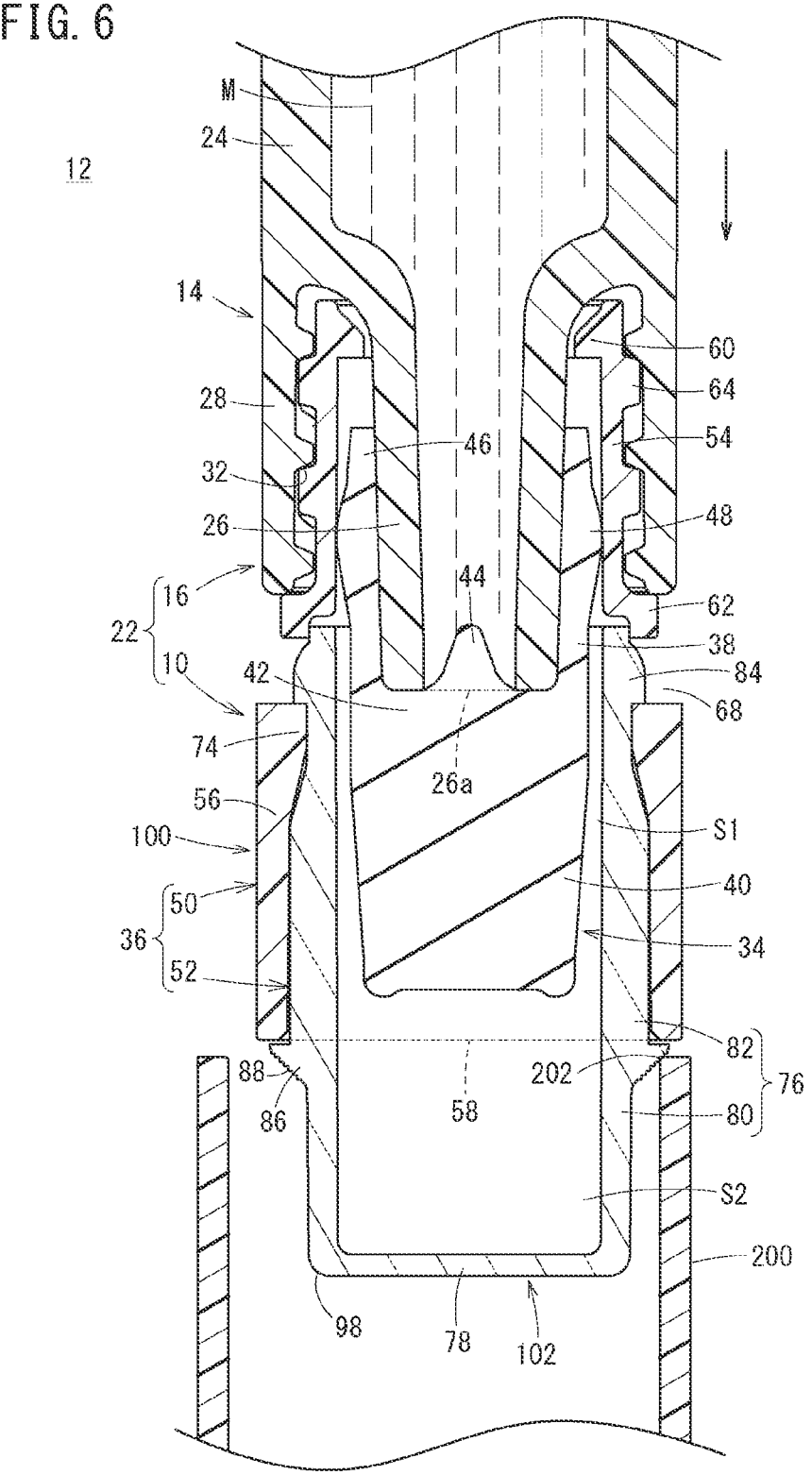
FIG. 6 is an explanatory cross-sectional view illustrating a state where the prefilled syringe is inserted into an insertion tube for conveyance.

Further, the plurality of stepped sections 88 can be arranged continuously along the center axis Ax of the cover member 36 such that a protruding amount of the tapered section 86 gradually increases from the outer peripheral surface of the annular peripheral wall section 80 toward a vicinity of the outer edge of the opening 58 of the first tubular section 100. As a result, as shown in FIG. 6, it is possible to prevent the tapered section 86 from being caught by an opening edge section 202 of an insertion tube 200 when the syringe assembly 22 (prefilled syringe 12) is inserted into the insertion tube 200 for conveyance. Therefore, the syringe assembly 22 can be rather easily inserted into the insertion tube 200 for conveyance.

In the cap 10, each of the plurality of stepped sections 88 has the first surface 90, the bent section 92 located at the outer edge of the first surface 90, and the second surface 94 extending in the proximal end direction from the bent section 92. The angle $\theta 1$ formed by the first surface 90 and the parallel straight line L1 parallel to the center axis Ax of the cover member 36 is larger than the taper angle $\theta 2$ formed by the parallel straight line L1 and the virtual straight line L2 passing through the distal end and the proximal end of the tapered section 86. The second surface 94 extends parallel to the center axis Ax.

According to such a configuration, when the user views the tapered section 86 from just beside, a refractive index of light on the second surface 94 of the tapered section 86 can be effectively reduced. Therefore, the viewing section 40 of the cap body 34 at the first position can be made further less visible when the user views the tapered section 86 from just beside in an unopened state of the cap 10.

In accordance with an exemplary embodiment, the taper angle $\theta 2$ can be, for example, 35° or more and 55° or less (i.e., 35° to 55°).

According to such a configuration, the syringe assembly 22 (prefilled syringe 12) can be rather easily inserted into the insertion tube 200 for conveyance.

Each of the plurality of stepped sections 88 includes the inclined surface 96 extending while being inclined outward from the proximal end of the second surface 94 and continuing to the inner edge of the first surface 90 of the stepped section 88 adjacent on the proximal end side.

According to such a configuration, the tapered section 86 can be effectively prevented from being caught by the opening edge section 202 of the insertion tube 200.

The bent section 92 has a curved surface protruding outward.

According to such a configuration, the tapered section 86 can be effectively prevented from being caught by the opening edge section 202 of the insertion tube 200.

In accordance with an exemplary embodiment, the second tubular section 102 is substantially transparent as a whole, and has the distal end curved surface 98 projecting outward between the outer edge of the distal end wall 78 and the annular peripheral wall section 80. A curvature radius of the distal end curved surface 98 is 0.3 mm or more and 1.0 mm or less (i.e., 0.3 mm to 1.0 mm).

According to such a configuration, since the entire second tubular section 102 is transparent, the user can rather easily visually recognize the viewing section 40 in a state where the cap 10 is remounted to the syringe body 14. In addition, it is possible to suppress a decrease in visibility of the viewing section 40 due to reflection of light on the distal end curved surface 98.

The cover member 36 includes the tubular section 56 constituting at least an outer peripheral section of the first tubular section 100 and being substantially opaque, and the cover member 36 having the second tubular section 102 and being substantially transparent.

According to such a configuration, the configuration of the substantially opaque first tubular section 100 and the substantially transparent second tubular section 102 can be simplified.

The distal end cover member 52 includes the extending inner tube section 82 that extends from the proximal end of the annular peripheral wall section 80 into the tubular section 56 and forms the inner peripheral section of the first tubular section 100. An inner diameter of the distal end cover member 52 is substantially uniform from the distal end of the annular peripheral wall section 80 to a proximal end of the extending inner tube section 82.

According to such a configuration, since a step is not substantially formed on the inner peripheral surface of the cover member 36 from the first space S1 to the second space S2, the cap body 34 can be rather smoothly displaced from the first position to the second position.

The cap 10, the syringe assembly 22, and the prefilled syringe 12 according to the present disclosure are not limited to the above-described embodiment, and it is a matter of course that various configurations can be adopted without departing from the gist of the present disclosure.

As illustrated in FIG. 7, a second surface 110 of the tapered section 86 may be inclined outward (radially outward) from the bent section 92 in the proximal end direction. In this case, an angle $\theta 1$ (first angle $\theta 1$) formed by the first surface 90 and the parallel straight line L1 parallel to the center axis Ax of the cover member 36 is larger than a taper angle $\theta 2$. An angle $\theta 3$ (second angle $\theta 3$) formed by the second surface 110 and a parallel straight line L3 parallel to the center axis Ax of the cover member 36 is smaller than the taper angle $\theta 2$.

That is, the first angle $\theta 1$, the taper angle $\theta 2$, and the second angle $\theta 3$ are set such that a relationship of $\theta 3 < \theta 2 < \theta 1$ is established. The first angle $\theta 1$ is preferably set, for example, to 60° or more and 90° or less (i.e., 60° to 90°). The taper angle $\theta 2$ is preferably set, for example, to 35° or more and 55° or less (i.e., 35° to 55°). The second angle θ3 is preferably set, for example, to 30° or less.

In the present embodiment, each of the plurality of stepped sections 88 has the first surface 90, the bent section 92 located at the outer edge of the first surface 90, and the second surface 110 extending in the proximal end direction from the bent section 92. The first angle θ1 is larger than the taper angle θ2, and the second angle θ3 is smaller than the taper angle θ2.

According to such a configuration, when the user views the tapered section 86 from just beside, a refractive index of light on the second surface 110 of the tapered section 86 can be effectively reduced. Therefore, the viewing section 40 of the cap body 34 at the first position can be made further less visible when the user views the tapered section 86 from just beside in an unopened state of the cap 10.

The present disclosure may be, for example, a prefilled syringe 12 having no plunger 20 (i.e., without a plunger 20). In this case, to the prefilled syringe 12, a pressing member that presses the gasket 18 in the distal end direction is separately mounted. In addition, the cap 10, the syringe assembly 22, or the prefilled syringe 12 in which the abutting protruding section 46 is omitted from the cap body 34 may be adopted. In this case, by making an inner diameter of the opening 58 on the proximal end side of the mounting tube section 38 smaller than a distal end outer diameter of the nozzle section 26 of the syringe outer tube 16, the proximal end of the mounting tube section 38 functions as an abutting section that can abut on the distal end section of the nozzle section 26.

Further, the cap body 34 may be configured such that the viewing section 40 does not include the distal end of the cap body 34, and the distal end of the cap body 34 protrudes to the distal end side from the opening 58 of the cap cover 50, at the first position. In this case, the viewing section 40 of the cap body 34 is provided so as to be located in the tubular section 56 of the cap cover 50 when the cap body 34 is at the first position, and to protrude from the opening 58 of the cap cover 50 when the cap body 34 is at the second position.

Examples of a viewing section 40 can include: a viewing section 40 formed by coloring an outer peripheral surface that is slightly on the proximal end side from the distal end of the cap body 34 in red or the like; and a viewing section 40 formed by a colored member fitted so as to cover an outer peripheral section that is slightly on the proximal end side from the distal end of the distal end protruding section of the cap body 34. Even with such a configuration, the user can rather easily and reliably discriminate between the unopened state and the recapped state of the cap 10.

In the distal end wall 78 of the distal end cover member 52, a hole having such a size that a user's finger cannot be inserted may be formed. In a case where such a hole is formed on the distal end wall 78, by inserting a jig into the hole of the distal end wall 78 and pushing the cap body 34 into the nozzle section 26, the previously assembled cap 10 can be mounted to the syringe outer tube 16.

Further, the cap 10 may be provided with a temporary fixing mechanism that performs temporary fixing to help prevent movement of the cap body 34 from the first position to the second position in a state where the cap 10 is removed from the syringe body 14. Examples of such a temporary fixing mechanism can include a temporary fixing protrusion provided on an inner peripheral surface of the cap cover 50 and engaged with a part of the cap body 34 arranged at the first position. In this case, an engagement force between the temporary fixing protrusion and the cap body 34 is set to be releasable by pressing the mounting section (mounting tube section 38) of the cap body 34 with the nozzle section 26 of the syringe body 14, which can help prevent the cap body 34 from being unintentionally displaced from the first position to the second position in the unopened state, and can displace the cap body 34 from the first position to the second position when the mounting section (mounting tube section 38) of the cap 10 removed from the syringe body 14 is brought close to the nozzle section 26 of the syringe body 14 in a state where the cap body 34 is arranged at the first position.

In accordance with an exemplary embodiment, in a state where the cap 10 is removed from the syringe body 14, the cap body 34 is movable from the first position to the second position without the mounting section (mounting tube section 38) being pushed by the nozzle section 26. Therefore, in a case where the cap 10 removed from the syringe body 14 is remounted to the syringe body 14 in a state where the cap body 34 is arranged at the second position, displacement of the cap body 34 from the first position to the second position does not occur. Even in this case, when the mounting section (mounting tube section 38) of the cap body 34 arranged at the second position abuts on the nozzle section 26, displacement of the cap body 34 from the second position to the first position can be regulated (or controlled), and the viewing section 40 is located at the second position. Therefore, the user can rather easily and reliably discriminate between the unopened state and the opened state of the cap 10.

In the above embodiment, a syringe cap 10 is disclosed that is detachable from a syringe body 14 including: a body section 24 capable of internally accommodating a drug M; and a nozzle section 26 protruding in a distal end direction from a distal end section of the body section 24 and having a drug discharge port 26a at a distal end, in which the syringe cap 10 includes: a cap body 34; and a tubular cover member 36 covering the cap body 34, the cap body 34 includes: a mounting section 38 having a sealing section 42 that liquid-tightly seals the drug discharge port 26a, and being mountable to the nozzle section 26; and a viewing section 40 located on a distal end side from the mounting section 38, the cover member 36 includes: an engagement section 60 provided on an inner peripheral surface of the cover member 36, and configured to engage with the cap body 34 to prevent detachment of the cap body 34 in a proximal end direction from the cover member 36; a first tubular section 100 being substantially opaque, and having an opening 58 at a distal end and a first space S1 capable of internally housing the viewing section 40; and a second tubular section 102 extending in a distal end direction from the opening 58 of the first tubular section 100, the second tubular section 102 includes: an annular peripheral wall section 80 extending in a distal end direction from the opening 58 of the first tubular section 100 and having an outer diameter smaller than an outer diameter of the first tubular section 100; a distal end wall 78 provided at a distal end of the annular peripheral wall section 80; a second space S2 defined by the annular peripheral wall section 80, the distal end wall 78, and the opening 58 of the first tubular section 100; and a tapered section 86 protruding from an outer peripheral surface of the annular peripheral wall section 80 toward a vicinity of an outer edge of the opening 58 of the first tubular section 100 so as to be inclined outward in a proximal end direction, at least the tapered section 86 and the annular peripheral wall section 80 of the second tubular section 102 are substantially transparent, the cap body 34 can displace, along a center axis Ax of the cover member 36 in the cover member 36, from a first position where the viewing section 40 is located in the first space S1 of the first tubular section 100 to a second position where the viewing section 40 protrudes in a distal end direction from the distal end of the first tubular section 100 to be arranged in the second space S2, an outer peripheral section of the viewing section 40 is substantially invisible when the cap body 34 is at the first position, and the outer peripheral section of the viewing section 40 becomes visible when the cap body 34 is at the second position, the sealing section 42 is capable of liquid-tightly sealing the nozzle section 26 in a state where the cap body 34 is located at the first position, in a state where the cap body 34 is arranged at the first position, when the mounting section 38 of the syringe cap 10 removed from the syringe body 14 is brought close to the nozzle section 26 of the syringe body 14, the mounting section 38 is pushed in a distal end direction by the nozzle section 26 of the syringe body 14 so as to displace the cap body 34 from the first position to the second position, and the tapered section 86 has, on an outer peripheral surface of the tapered section 86, a plurality of stepped sections 88 continuously arranged along the center axis Ax of the cover member 36, so as to gradually increase a protruding amount of the tapered section 86 from an outer peripheral surface of the annular peripheral wall section 80 toward a vicinity of the outer edge of the opening 58 of the first tubular section 100.

In the syringe cap 10 described above, each of the plurality of stepped sections 88 may have a first surface 90, a bent section 92 located at an outer edge of the first surface 90, and a second surface 94 extending in a proximal end direction from the bent section 92. A first angle θ1 formed by the first surface 90 and a parallel straight line L1 parallel to the center axis Ax of the cover member 36 may be larger than a taper angle θ2 formed by the parallel straight line L1 and a virtual straight line L2 passing through a distal end and a proximal end of the tapered section 86, and a second angle θ3 formed by the second surface 94 and a parallel straight line L3 parallel to the center axis Ax of the cover member 36 may be smaller than the taper angle θ2.

In the syringe cap 10 described above, each of the plurality of stepped sections 88 may have a first surface 90, a bent section 92 located at an outer edge of the first surface 90, and a second surface 94 extending in a proximal end direction from the bent section 92. An angle θ1 formed by the first surface 90 and a parallel straight line L1 parallel to the center axis Ax of the cover member 36 may be larger than a taper angle θ2 formed by the parallel straight line L1 and a virtual straight line L2 passing through the distal end and the proximal end of the tapered section 86, and the second surface 94 may extend parallel to the center axis Ax.

In the syringe cap 10 described above, the taper angle θ2 may be, for example, 35° or more and 55° or less (i.e., 35° to 55°).

In the syringe cap 10 described above, the first angle θ1 may be, for example, 60° or more and 90° or less (i.e., 60° to 90°), and the second angle θ3 may be, for example, 30° or less.

In the syringe cap 10 described above, each of the plurality of stepped sections 88 may have an inclined surface 96 extending while being inclined outward from a proximal end of the second surface 94 and continuing to an inner edge of the first surface 90 of a stepped section 88 adjacent on the proximal end side.

In the syringe cap 10 described above, the bent section 92 may have a curved surface protruding outward.

In the syringe cap 10 described above, the second tubular section 102 may be substantially transparent as a whole and have a distal end curved surface 98 protruding outward between an outer edge of the distal end wall 78 and the annular peripheral wall section 80, and a curvature radius of the distal end curved surface 98 may be, for example, 0.3 mm or more and 1.0 mm or less (i.e., 0.3 mm to 1.0 mm).

In the syringe cap 10 described above, the cover member 36 may include a tubular section 56 constituting at least an outer peripheral section of the first tubular section 100 and being substantially opaque, and a distal end cover member 52 having the second tubular section 102 and being substantially transparent.

In the syringe cap 10 described above, the distal end cover member 52 may have an extending inner tube section 82 that extends from a proximal end of the annular peripheral wall section 80 into the tubular section 56 and forms an inner peripheral section of the first tubular section 100, and an inner diameter of the distal end cover member 52 may be substantially uniform from a distal end of the annular peripheral wall section 80 to a proximal end of the extending inner tube section 82.

In the syringe cap 10 described above, the syringe body 14 may include a lock adapter 28 having a tubular shape, having a female screw section 32 on an inner peripheral surface, and covering an outer peripheral section of the nozzle section 26, the mounting section 38 may be a mounting tube section 38 having a tubular shape and being capable of accommodating the nozzle section 26, the mounting tube section 38 may have: the sealing section 42 located at a distal end section of the mounting tube section 38; and an abutting section 46 located at a proximal end section of the mounting tube section 38 and being capable of abutting on a distal end section of the nozzle section 26, the cover member 36 may have a tubular connecting section 54 that extends in a proximal end direction from a proximal end of the first tubular section 100 and can be inserted between the lock adapter 28 and the nozzle section 26, the tubular connecting section 54 may have, on an outer peripheral section of the tubular connecting section 54, a male screw section 64 capable of being screwed with the female screw section 32 of the lock adapter 28, in a state where the syringe cap 10 is mounted to the syringe body 14 by screwing between the male screw section 64 of the tubular connecting section 54 and the female screw section 32 of the lock adapter 28, and the cap body 34 is located at the first position, the mounting tube section 38 may be inserted between the tubular connecting section 54 and the nozzle section 26, and the sealing section 42 may liquid-tightly seal the drug discharge port 26a, and when the male screw section 64 of the tubular connecting section 54 is screwed with the female screw section 32 of the lock adapter 28 in a state where the syringe cap 10 is removed from the syringe body 14, the cap body 34 may be displaced from the first position to the second position by the abutting section 46 of the cap body 34 being pushed by the distal end section of the nozzle section 26.

The above embodiment discloses a syringe assembly 22 including the syringe cap 10 described above and a syringe outer tube 16 constituting the syringe body 14 and being capable of accommodating a drug M.

The above embodiment discloses a prefilled syringe 12 including the syringe assembly 22 described above, a drug M filled in the syringe outer tube 16, and a gasket 18 liquid-tightly slidable in the syringe outer tube 16 in an axial direction.

The detailed description above describes embodiments of a syringe cap, a syringe assembly, and a prefilled syringe, in which the syringe cap is detachably attachable to a syringe body that includes a body section capable of internally accommodating a drug, and a nozzle section protruding in a distal end direction from a distal end section of the body section and having a drug discharge port at a distal end. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A syringe cap configured to be detachable from and attachable to a syringe body, the syringe body including a body section configured to accommodate a drug, and a nozzle section protruding in a distal end direction from a distal end section of the body section and having a drug discharge port at a distal end, the syringe cap comprising:
   a cap body;
   a cover member having a tubular shape and covering the cap body;
   the cap body includes:
      a mounting section including a sealing section that liquid-tightly seals the drug discharge port and being mountable to the nozzle section; and
      a viewing section located on a distal end side from the mounting section;
   the cover member includes:
      an engagement section provided on an inner peripheral surface of the cover member, and configured to engage with the cap body to prevent detachment of the cap body in a proximal end direction from the cover member;
      a first tubular section being substantially opaque, and having an opening at a distal end and a first space capable of internally housing the viewing section; and
      a second tubular section extending in a distal end direction from the opening of the first tubular section;
   the second tubular section includes:
      an annular peripheral wall section extending in a distal end direction from the opening of the first tubular section and having an outer diameter smaller than an outer diameter of the first tubular section;
      a distal end wall provided at a distal end of the annular peripheral wall section;
      a second space defined by the annular peripheral wall section, the distal end wall, and the opening of the first tubular section; and
      a tapered section protruding from an outer peripheral surface of the annular peripheral wall section toward a vicinity of an outer edge of the opening of the first tubular section so as to be inclined outward in a proximal end direction;
   at least the tapered section and the annular peripheral wall section of the second tubular section are substantially transparent;
   the cap body is configured to be displaced, along a center axis of the cover member in the cover member, from a first position where the viewing section is located in the first space of the first tubular section to a second position where the viewing section protrudes in a distal end direction from the distal end of the first tubular section to be arranged in the second space;
   an outer peripheral section of the viewing section is not visible when the cap body is at the first position, and the outer peripheral section of the viewing section becomes visible when the cap body is at the second position;
   the sealing section is capable of liquid-tightly sealing the nozzle section in a state where the cap body is located at the first position;
   in a state where the cap body is arranged at the first position, when the mounting section of the syringe cap removed from the syringe body is brought close to the nozzle section of the syringe body, the mounting section is pushed in a distal end direction by the nozzle section of the syringe body so as to displace the cap body from the first position to the second position; and
   the tapered section has, on an outer peripheral surface of the tapered section, a plurality of stepped sections continuously arranged along the center axis of the cover member, so as to gradually increase a protruding amount of the tapered section from an outer peripheral surface of the annular peripheral wall section toward a vicinity of the outer edge of the opening of the first tubular section.

2. The syringe cap according to claim 1, wherein
   each of the plurality of stepped sections has a first surface, a bent section located at an outer edge of the first surface, and a second surface extending in a proximal end direction from the bent section;
   a first angle formed by the first surface and a parallel straight line parallel to the center axis of the cover member is larger than a taper angle formed by the parallel straight line and a virtual straight line passing through a distal end and a proximal end of the tapered section; and
   a second angle formed by the second surface and a parallel straight line parallel to the center axis of the cover member is smaller than the taper angle.

3. The syringe cap according to claim 1, wherein
   each of the plurality of stepped sections has a first surface, a bent section located at an outer edge of the first surface, and a second surface extending in a proximal end direction from the bent section;
   an angle formed by the first surface and a parallel straight line parallel to the center axis of the cover member is larger than a taper angle formed by the parallel straight line and a virtual straight line passing through a distal end and a proximal end of the tapered section; and
   the second surface extends parallel to the center axis.

4. The syringe cap according to claim 2, wherein the taper angle is 35° to 55°.

5. The syringe cap according to claim 4, wherein the first angle is 60° to 90°, and the second angle is 30° or less.

6. The syringe cap according to claim 2, wherein each of the plurality of stepped sections includes an inclined surface extending while being inclined outward from a proximal end of the second surface and continuing to the inner edge of the first surface of a stepped section adjacent on a proximal end side.

7. The syringe cap according to claim 2, wherein the bent section has a curved surface protruding outward.

8. The syringe cap according to claim 2, wherein
   the second tubular section is substantially transparent as a whole and has a distal end curved surface protruding outward between an outer edge of the distal end wall and the annular peripheral wall section, and
   a curvature radius of the distal end curved surface is 0.3 mm to 1.0 mm.

9. The syringe cap according to claim 1, wherein the cover member includes a tubular section constituting at least an outer peripheral section of the first tubular section and being substantially opaque, and a distal end cover member having the second tubular section and being substantially transparent.

10. The syringe cap according to claim 9, wherein
the distal end cover member has an extending inner tube section that extends from a proximal end of the annular peripheral wall section into the tubular section and forms an inner peripheral section of the first tubular section; and
an inner diameter of the distal end cover member is substantially uniform from a distal end of the annular peripheral wall section to a proximal end of the extending inner tube section.

11. The syringe cap according to claim 1, wherein
the syringe body includes a lock adapter having a tubular shape, having a female screw section on an inner peripheral surface, and covering an outer peripheral section of the nozzle section;
the mounting section is a mounting tube section having a tubular shape and being capable of accommodating the nozzle section;
the mounting tube section includes the sealing section located at a distal end section of the mounting tube section and an abutting section located at a proximal end section of the mounting tube section and being capable of abutting with a distal end section of the nozzle section;
the cover member has a tubular connecting section that extends in a proximal end direction from a proximal end of the first tubular section and is capable of being inserted between the lock adapter and the nozzle section;
the tubular connecting section has a male screw section capable of being screwed with the female screw section of the lock adapter, on an outer peripheral section of the tubular connecting section;
in a state where the syringe cap is mounted to the syringe body by screwing between the male screw section of the tubular connecting section and the female screw section of the lock adapter, and the cap body is located at the first position, the mounting tube section is inserted between the tubular connecting section and the nozzle section, and the sealing section liquid-tightly seals the drug discharge port; and
when the male screw section of the tubular connecting section is screwed with the female screw section of the lock adapter in a state where the syringe cap is removed from the syringe body, the cap body is displaced from the first position to the second position by the abutting section of the cap body being pushed by the distal end section of the nozzle section.

12. A syringe assembly comprising:
the syringe cap according to claim 1; and
a syringe outer tube constituting the syringe body and configured to accommodate the drug.

13. A prefilled syringe comprising:
the syringe assembly according to claim 12;
the drug filled in the syringe outer tube; and
a gasket liquid-tightly slidable in the syringe outer tube in an axial direction.

14. A syringe cap configured to be detachable from and attachable to a syringe body, the syringe cap comprising:
a cap body, the cap body includes:
a mounting section including a sealing section configured to seal a drug discharge port on the syringe body and configured to be mounted to a nozzle section of the syringe body; and
a viewing section located on a distal end side from the mounting section;
a cover member having a tubular shape and covering the cap body, the cover member includes:
an engagement section provided on an inner peripheral surface of the cover member, and the cover member being configured to engage with the cap body;
a first tubular section having an opening at a distal end and a first space capable of internally housing the viewing section; and
a second tubular section extending in a distal end direction from the opening of the first tubular section;
the second tubular section includes:
an annular peripheral wall section extending in a distal end direction from the opening of the first tubular section and having an outer diameter smaller than an outer diameter of the first tubular section;
a distal end wall provided at a distal end of the annular peripheral wall section;
a second space defined by the annular peripheral wall section, the distal end wall, and the opening of the first tubular section; and
a tapered section protruding from an outer peripheral surface of the annular peripheral wall section toward a vicinity of an outer edge of the opening of the first tubular section so as to be inclined outward in a proximal end direction;
the tapered section has, on an outer peripheral surface of the tapered section, a plurality of stepped sections continuously arranged along the center axis of the cover member, so as to gradually increase a protruding amount of the tapered section from an outer peripheral surface of the annular peripheral wall section toward a vicinity of the outer edge of the opening of the first tubular section; and
wherein the cap body is configured to be displaced, along a center axis of the cover member in the cover member, from a first position where the viewing section is located in the first space of the first tubular section to a second position where the viewing section protrudes in a distal end direction from the distal end of the first tubular section to be arranged in the second space.

15. The syringe cap according to claim 14, wherein at least the tapered section and the annular peripheral wall section of the second tubular section are transparent.

16. The syringe cap according to claim 14, wherein
an outer peripheral section of the viewing section is not visible when the cap body is at the first position, and the outer peripheral section of the viewing section becomes visible when the cap body is at the second position;
the sealing section configured to be seal the nozzle section of the syringe body in a state where the cap body is located at the first position;
in a state where the cap body is arranged at the first position, when the mounting section of the syringe cap removed from the syringe body is brought close to the nozzle section of the syringe body, the mounting section is pushed in a distal end direction by the nozzle section of the syringe body so as to displace the cap body from the first position to the second position.

17. The syringe cap according to claim 16, wherein each of the plurality of stepped sections has a first surface, a bent section located at an outer edge of the first surface, and a second surface extending in a proximal end direction from the bent section;
a first angle formed by the first surface and a parallel straight line parallel to the center axis of the cover member is larger than a taper angle formed by the parallel straight line and a virtual straight line passing through a distal end and a proximal end of the tapered section; and
a second angle formed by the second surface and a parallel straight line parallel to the center axis of the cover member is smaller than the taper angle.

18. A syringe assembly, the syringe assembly comprising:
a syringe body, the syringe body including a body section configured to accommodate a drug, and a nozzle section protruding in a distal end direction from a distal end section of the body section and having a drug discharge port at a distal end;
a syringe cap configured to be detachable from and attachable to the syringe body, the syringe cap comprising:
    a cap body, the cap body includes:
        a mounting section including a sealing section configured to seal a drug discharge port on the syringe body and configured to be mounted to a nozzle section of the syringe body; and
        a viewing section located on a distal end side from the mounting section;
    a cover member having a tubular shape and covering the cap body, the cover member includes:
        an engagement section provided on an inner peripheral surface of the cover member, and the cover member being configured to engage with the cap body;
        a first tubular section having an opening at a distal end and a first space capable of internally housing the viewing section; and
        a second tubular section extending in a distal end direction from the opening of the first tubular section;
    the second tubular section includes:
        an annular peripheral wall section extending in a distal end direction from the opening of the first tubular section and having an outer diameter smaller than an outer diameter of the first tubular section;
        a distal end wall provided at a distal end of the annular peripheral wall section;
        a second space defined by the annular peripheral wall section, the distal end wall, and the opening of the first tubular section; and
        a tapered section protruding from an outer peripheral surface of the annular peripheral wall section toward a vicinity of an outer edge of the opening of the first tubular section so as to be inclined outward in a proximal end direction; and
    the tapered section has, on an outer peripheral surface of the tapered section, a plurality of stepped sections continuously arranged along the center axis of the cover member, so as to gradually increase a protruding amount of the tapered section from an outer peripheral surface of the annular peripheral wall section toward a vicinity of the outer edge of the opening of the first tubular section; and
wherein the cap body is configured to be displaced, along a center axis of the cover member in the cover member, from a first position where the viewing section is located in the first space of the first tubular section to a second position where the viewing section protrudes in a distal end direction from the distal end of the first tubular section to be arranged in the second space.

19. A prefilled syringe comprising:
the syringe assembly according to claim 18;
the drug filled in the syringe body; and
a gasket liquid-tightly slidable in the syringe body in an axial direction.

* * * * *